United States Patent [19]

Jones

[11] Patent Number: 4,644,683
[45] Date of Patent: Feb. 24, 1987

[54] METHOD AND APPARATUS FOR ENHANCING THE POLLINATION OF ALFALFA

[76] Inventor: Darrell R. Jones, 14010 NW. 36th Ave., Vancouver, Wash. 98685

[21] Appl. No.: 754,170

[22] Filed: Jul. 12, 1985

[51] Int. Cl.⁴ .......................... A01G 13/06; F24H 3/04
[52] U.S. Cl. ......................................... 47/1.41; 47/2; 244/136; 432/222
[58] Field of Search ...................... 47/1.41, 2, DIG. 1; 126/59.5; 244/136, 137 R; 239/171; 432/222–224, 212; 431/351

[56] References Cited

U.S. PATENT DOCUMENTS

| | | | |
|---|---|---|---|
| 2,606,014 | 8/1952 | Baumann | 432/222 |
| 3,377,743 | 4/1968 | Thompson et al. | 126/59.5 |
| 3,481,405 | 12/1969 | Ward | 239/171 |
| 3,681,900 | 8/1972 | Blevins | 239/171 |
| 3,755,962 | 9/1973 | Walters et al. | 244/136 |
| 3,881,863 | 5/1975 | Creuz | 432/222 |
| 4,201,544 | 5/1980 | Briggs et al. | 432/222 |
| 4,532,914 | 8/1985 | Thomas et al. | 432/222 |

FOREIGN PATENT DOCUMENTS

| | | | |
|---|---|---|---|
| 1183961 | 7/1959 | France | 239/171 |
| 1209240 | 10/1967 | United Kingdom | 47/1.41 |
| 470287 | 8/1975 | U.S.S.R. | 47/1.41 |
| 490438 | 2/1976 | U.S.S.R. | 47/1.41 |

OTHER PUBLICATIONS

Anon., "The Farm Surplus You're Paying For", *Life*, vol. 27 (22) Nov. 30, 1959 (p. 28 only).
Bass, Ralph, "Flying Buzz Saw", *This Week, Sunday Star*, Apr. 24, 1949, p. 15.
Author unknown, "Kamov Ka-26 Tests Aerial Pollination Dusting Technique", Publication, Date, page unknown.

*Primary Examiner*—James R. Feyrer
*Attorney, Agent, or Firm*—Klarquist, Sparkman, Campbell, Leigh & Whinston

[57] ABSTRACT

Pollination of alfalfa enhanced by flying a helicopter over a field of alfalfa with propane burners mounted on the helicopter and directed to heat air in vicinity of alfalfa blossoms. Heat causes blossoms to open and agitation by downdraft enhances spread of pollen through field to increase pollination and seed yield.

6 Claims, 9 Drawing Figures

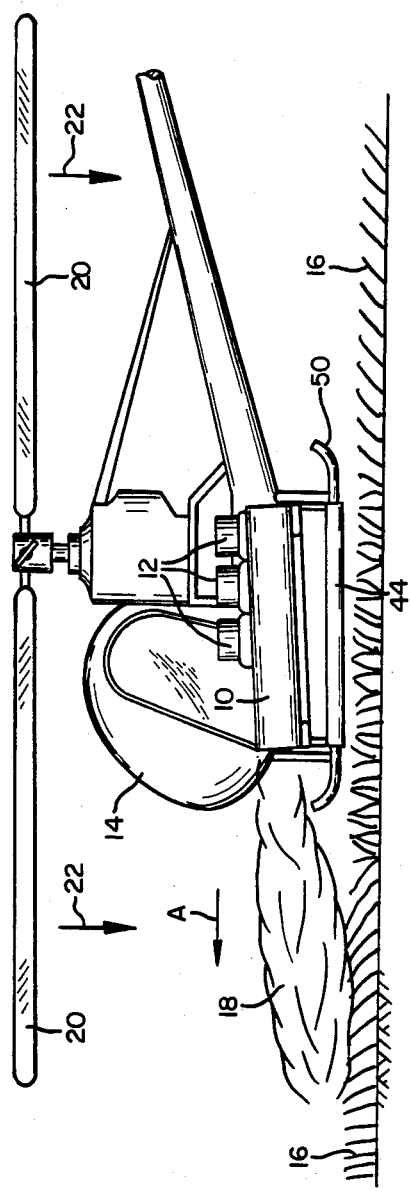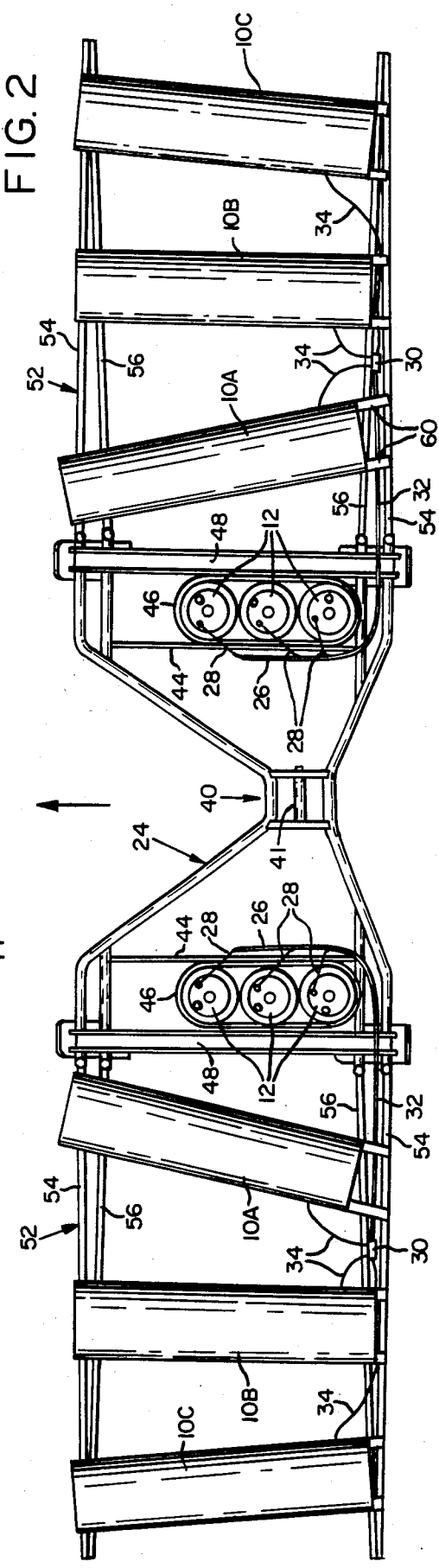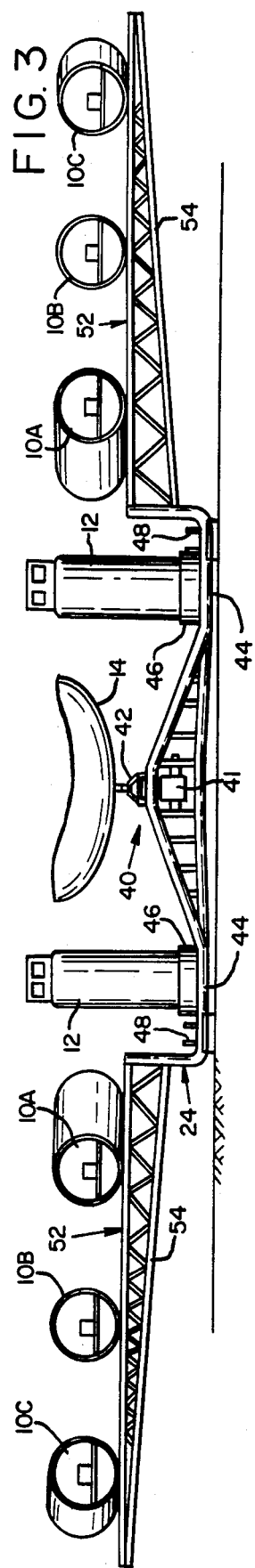

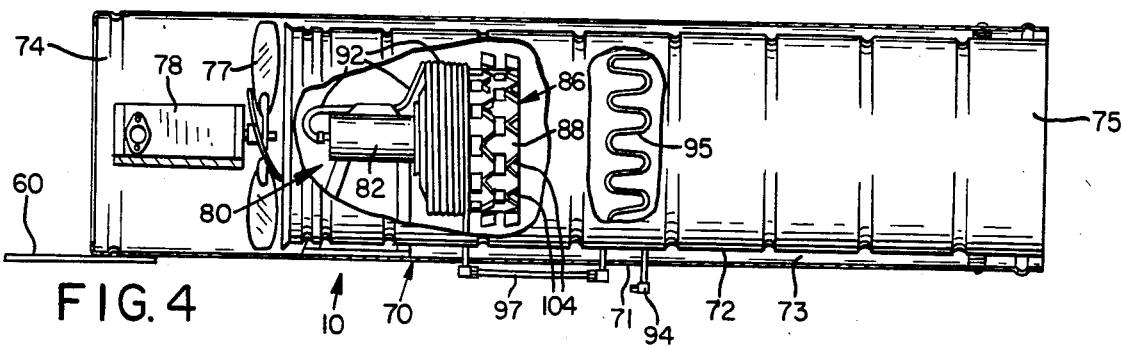
FIG. 4
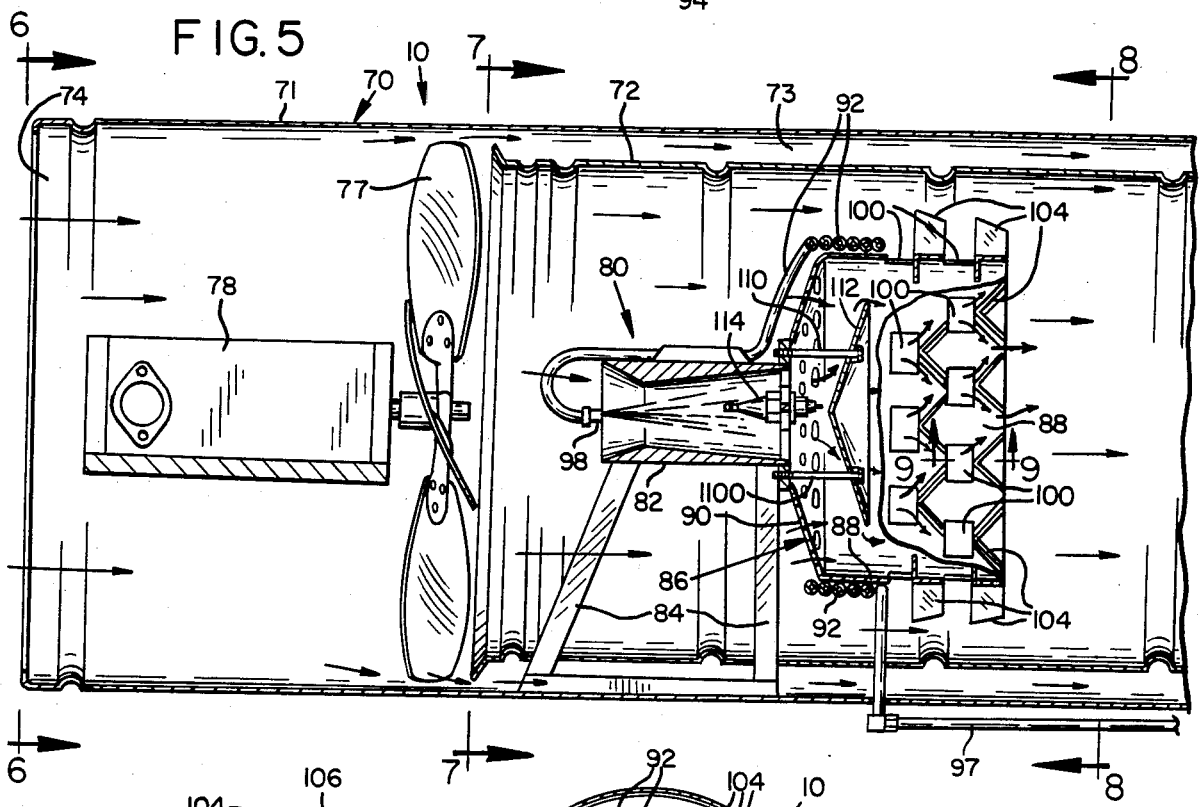
FIG. 5
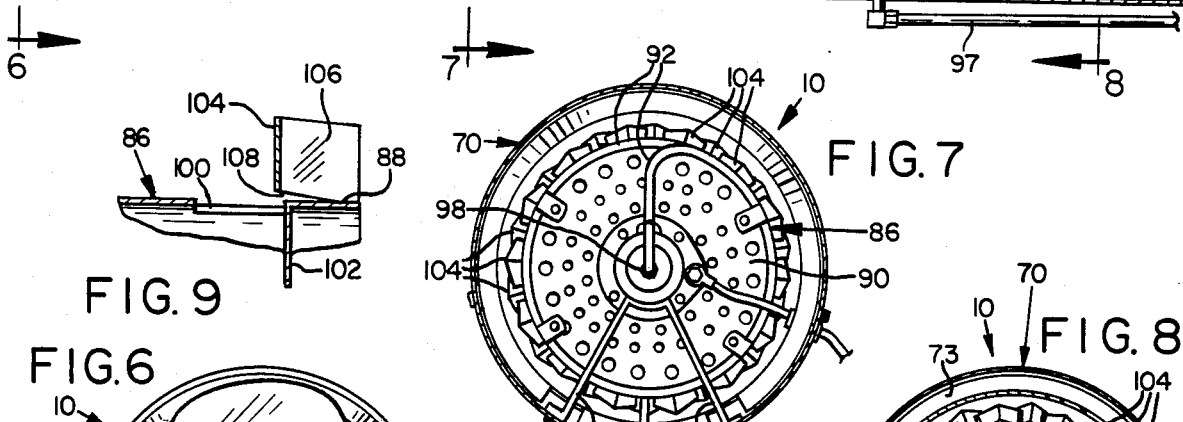
FIG. 9
FIG. 7
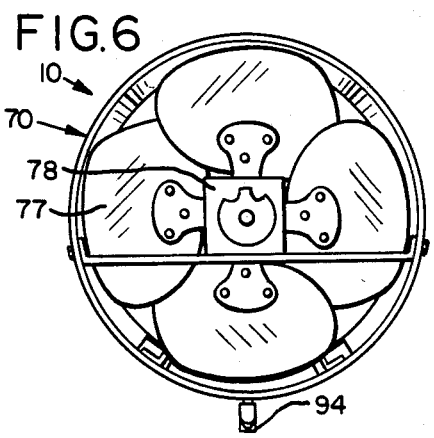
FIG. 6
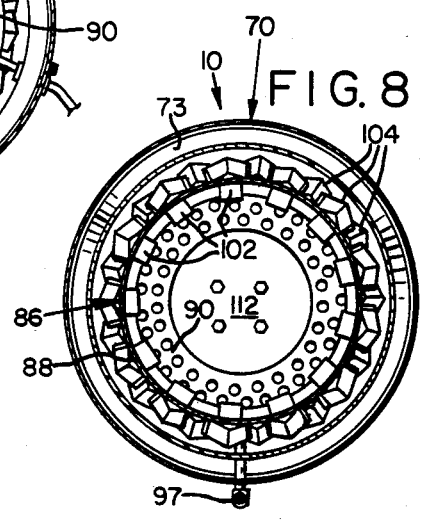
FIG. 8

METHOD AND APPARATUS FOR ENHANCING THE POLLINATION OF ALFALFA

BACKGROUND OF THE INVENTION

1. Field of the Invention

This invention relates generally to heating the atmosphere over a field crop, and more particularly to utilizing a heat source to enhance alfalfa pollination.

2. Description of the Prior Art

Heating of the atmosphere over a field crop is desirable at times such as to prevent frost damage or to enhance pollination in alfalfa fields. For the former, smudge pots have been utilized to lay down an insulating blanket of smoke. In some instances heaters have been used with fixed adjacent fans to distribute the heat. Both systems have their drawbacks.

Pollination of alfalfa for production of seed is generally accomplished haphazardly by the wind, although pollination is also accomplished utilizing leaf-cutter bees.

It is desirable to increase the degree of pollination in order to increase the production of mature alfalfa seed. The greatest degree of pollination is known to occur on hot, dry days. The heat from the sun causes the alfalfa blossoms to open more readily, exposing more pollen to the wind or bees. The lower the relative humidity, the more easily is pollen transferred throughout the crop by wind or bees.

Attempts have been made to increase alfalfa seed yield by mechanical agitation of the crop to increase pollination, but such attempts have been unsuccessful. For example, chains or netting material have been pulled with a tractor through an alfalfa crop in an effort to transfer more pollen from the stamens to the stigmas of alfalfa blossoms, thereby to increase seed yields. These and other such methods generally result in trampling and ultimate damage to the crop. Relying on the wind and bees to transfer pollen has proven to be unreliable and unpredictable.

Accordingly, there remains a need for a reliable method for increasing the pollination of alfalfa over that presently obtainable through natural means.

SUMMARY OF THE INVENTION

An object of the present invention is to provide an improved means for heating uniformly the atmosphere over a field crop.

A more particular object of the present invention is to increase alfalfa seed yield by providing a more reliable method for enhancing the pollination of alfalfa.

Another object of the present invention is to provide a method and apparatus for enhancing alfalfa pollination which will not damage the alfalfa crop.

These and other objects of the invention will become apparent from the ensuing drawings and detailed description.

BRIEF DESCRIPTION OF THE DRAWINGS

FIG. 1 is a side view of a helicopter with the apparatus of the invention attached showing the same in operation positioned over an alfalfa field;

FIG. 2 is a top view of the apparatus of the invention showing the same removed from the helicopter;

FIG. 3 is a rear view of the apparatus shown in FIG. 2;

FIG. 4 is a side elevation, partially broken away, of a propane burner utilized in the apparatus;

FIG. 5 is an enlarged, fragmentary view, partially in section, of a portion of the propane burner shown in FIG. 4;

FIG. 6 is a sectional view of the intake end of a propane burner, taken along lines 6—6 in FIG. 5;

FIG. 7 is a sectional view of the burner taken along lines 7—7 in FIG. 5;

FIG. 8 is a sectional view of the burner taken along lines 8—8 in FIG. 5;

and FIG. 9 is an enlarged sectional view taken along lines 9—9 of FIG. 5.

DETAILED DESCRIPTION OF THE DRAWINGS

With reference to FIG. 1, a helicopter 14 equipped with propane burners 10 on each side and propane tanks 12 to fuel the burners is shown flying over alfalfa crop 16 in a forward, horizontal line of travel indicated by the arrow A. The propane burners 10 are angled slightly downward, producing a blast of heated air 18 at the surface of the alfalfa crop 16. The burners 10 are constructed and operated so that helicopter 14 can be flown at an altitude of between 3 and 6 feet above the alfalfa crop 16 such that the heated blast of air 18 produces a temperature at the alfalfa surface of approximately 110° F. This causes the alfalfa blossoms (not shown) fully to open and expose the pollen located therein. Helicopter rotor blades 20 create a downward blast of turbulent air 22 which spreads the pollen in the alfalfa blossoms throughout the crop and thereby increases the degree of pollination and, finally, the yield of mature alfalfa seed.

Referring to FIG. 2 in the illustrated embodiment, three propane burners 10A, 10B, 10C and propane tanks 12 are mounted on each side of a frame 24 extending outwardly on each side of the helicopter. Inboard propane burners 10A are angled in towards the line of travel A, the center propane burners 10B are aligned parallel to the line of travel A, while the outboard propane burners 10C are angled slightly away from the line of travel A so as evenly to heat the crop as the helicopter passes over a field. Propane is fed from the propane tanks 12 to a fuel manifold 26 through fuel lines 28. Propane is fed from the fuel manifold 26 to a fuel distributor 30 through fuel lines 32, and from there to burners 10A, 10B, and 10C through fuel lines 34.

Referring to FIGS. 2 and 3, the framework 24 includes a center section 40 in the center of which is provided an eye 41 for receiving a conventional drop hook 42 provided on the helicopter. The center section 40 provides a platform 44 on each side thereof on which are mounted retaining frames 46 in which the tanks set as best shown in FIG. 3. Additional means (not shown) may be provided additionally to brace the tanks 12 and prevent their tipping.

The platforms 44 are each provided with a channel 48 extending fore and aft outwardly of the rings 46 and into which the skids 50 of the helicopter are adapted to seat.

The frame 24 also includes laterally extending support portions 52 on each side of the center section, each comprising a pair of cantilevered parallel trusses 54. Each of the trusses is braced by a diagonal brace 56 to maintain the trusses in parallel relation. The burners 10A, 10B and 10C are secured to the trusses 54 by suitable means including brackets 60 extending from the burner housing at the inlet end and suitable brackets (not shown) extending between the housing at the outlet end and the adjacent truss. The frame 24 is preferably made of tubing so as to provide sufficient structural strength with the least possible weight.

Referring now to FIGS. 4-8, inclusive, each burner comprises a tubular housing 70 comprising an outer shell 71 and an inner liner 72 spaced therefrom to define an air flow channel 73. The housing 70 has an inlet end 74 and an outlet end 75. Mounted within the housing adjacent the inlet end 74 is a fan 77 driven by an electric motor 78 adapted to be supplied with power by suitable leads (not shown) from the power supply of the helicopter 14. The liner 72 terminates downstream from the fan 77 so that the fan, when operating, may provide a draft of cooling air through the channel 73.

The burner unit 80 includes a venturi element 82 which is supported from the housing 70 on legs 84. Mounted to the venturi element 82 is a shroud 86 having a cylindrical flange 88 extending coaxially from the disked base portion 90 of the shroud. The base portion is perforated to permit the flow of air therethrough and through the shroud. Fuel, preferably liquid propane, for the burner is fed through a suitable inlet line to a coupler 94 for an internal fuel line having a primary expansion coil 95 secured to the inner periphery of the liner 72 forwardly of the burner unit 80 so that it will receive some of the heat from the burner unit to assist in evaporation of the propane. A secondary expansion coil 92 is wrapped around the flange 88 further to assist in the evaporation of the fuel, the coils being interconnected by a fuel line portion 97. From the coil the fuel line extends to a burner nozzle 98 positioned in the venturi element 82. Beyond the coil 92 the shroud is formed with a plurality of openings 100 and inwardly projecting baffles 102. The baffles 102 and openings 100 can be provided by forming a three sided rectangular cut in the shroud and bending the cut portion inwardly.

Secured to the outer surface of the baffle, one adjacent each opening 100, downstream from such baffle is a triangular deflector 104, the apex of which is adjacent the downstream edge of the opening. Preferably the deflectors are formed so that the apex and the upstream portion of the sides 106 of the deflector are positioned slightly spaced from the periphery of the shroud 86 to provide an opening 108 (FIG. 9) through which air escaping through the adjacent opening 100 may flow.

Mounted in the outlet end of the venturi 82 by suitable means is a spark igniter 114. Supported from the base portion 90 of the shroud by legs 110 is a conical baffle plate 112.

OPERATION

When the unit is to be used the helicopter 14 is positioned on the frame 24 with the helicopter skids positioned in the channels 48. The quick release coupling of the helicopter is then connected to the eye 41 and the conventional lift winch operated to tension the coupling connection to the frame. Thereafter the electrical leads for the valve controls for the fuel lines, spark igniters and fan motors 78 are connected.

The helicopter is then operated to lift the frame and associated equipment and flown over the alfalfa field which is ready for treatment. Upon ignition of the propane burners, propane flows through the propane fuel line to nozzle 98 where it is released into venturi section 82. Air propelled by the fan 77 also enters venturi section 82, where it mixes with the propane gas, forming a fuel mixture. This mixture is ignited by energizing the spark igniter 114. The burning mixture is propelled by the fan blast out of the venturi and against the baffle plate 112 which will deflect the gas towards its periphery around which it will flow and thence along the inner periphery of the shroud 86. The inwardly projecting baffles 102 create a turbulent condition within the shroud assuring an intimate mixture of air and fuel to promote complete burning. In addition, the baffles 102 deflect some of the fuel-air mixture and combustion products outwardly through the openings 100. The deflectors 104 further assist in securing an intimate mixture of air and fuel. As a result of this thorough mixing, the fuel is completely burned within the burner. The fuel-air ratio is controlled so the exiting products will have a temperature of between about 600 degrees F. and 800 degrees F. The temperature of the exhaust gases and advance rate of the helicopter 14 is preferably controlled so that the temperature of the heated atmosphere in the vicinity of the blossoms will be between about 100 degrees F. to 120 degrees F. The helicopter is advanced over the field to be treated at an elevation of between about 3 and 6 feet above the crop. As indicated earlier, the forwardly projecting blasts of heated air from the burners causes the blossoms to open. Thence, as the helicopter passes over the opened blossoms, the agitation of the blossoms from the rotor draft causes the pollen in the blossoms to be spread to effect a more complete pollenization than would normally occur.

While the invention has been described with particular respect to the pollination of alfalfa, it will be recognized that the apparatus and techniques may be employed to heat the atmosphere over a field for other purposes as, for example, to prevent frost damage.

I claim:

1. A method for increasing the production of mature alfalfa seed by enhancing the pollination of alfalfa comprising:

providing a heat source on a helicopter;

flying the helicopter over a field of alfalfa and directing the heat from said source forwardly of the helicopter flight path so as to increase the ambient temperature and reduce relative humidity adjacent the alfalfa blossoms sufficient to cause them fully to open; and thereafter causing the downdraft from the blades on said helicopter to agitate the opened blossoms, thereby causing spreading of the pollen throughout the alfalfa crop to effect an increase in the production of mature alfalfa seed.

2. An apparatus for heating the atmosphere comprising:

a helicopter;

a heat source mounted to a frame structure depending from said helicopter for providing a flow of heated air forwardly of said helicopter's main rotor's axis of rotation;

and control means in said helicopter connected to said heat source for controlling the same.

3. The apparatus of claim 2 wherein the heat source comprises propane burners laterally mounted on each side of the helicopter in a horizontal row.

4. An apparatus for heating the atmosphere comprising:

a helicopter;

a frame adapted to be connected to the underside of said helicopter and extending outwardly on each side of said helicopter;

a heat source mounted on said helicopter for providing a flow of heated air forwardly of said helicopter, said heat source comprising a plurality of burners mounted on said frame on each side thereof;

said burners including means for burning a fuel supplied thereto and means for causing a flow of the heated gases from said burner in a direction forwardly of the flight path of said helicopter;

means on said frame for supporting a supply of fuel for said burners;

means for connecting said fuel supply to said burners; and control means in said helicopter operatively connected to said burners for controlling the operation of the same.

5. A burner adapted for use in heating the atmosphere comprising:

a tubular housing having an inlet end and an outlet end;

a fan mounted in said housing adjacent the inlet end for causing a flow of air therethrough;

a burner unit immediately downstream of said fan for burning a fluid fuel, said burner unit comprising a venturi means mounted coaxially of said fan and a nozzle through which said fuel is fed into said venturi at the throat thereof;

and baffle means in said housing downstream of said venturi for effecting thorough mixing of the combustion products of the fuel ejected from said nozzle with air flowing from said fan;

said baffle means comprising a perforated conical plate mounted at the rear edge of the venturi and of lesser diameter than said housing, and a baffle plate mounted rearwardly and coaxially of said venturi for diverting at least a portion of said combustion products outwardly toward said housing;

a tubular shroud mounted coaxially of said housing downstream of said plate, said shroud having a plurality of openings therethrough and baffle plates extending inwardly from the inner surface thereof for intercepting the flow of gases along the inner surface of said shroud and causing intermixing of the same, and deflecting at least a portion of said products and air outwardly through said openings;

and a plurality of further baffles mounted on and projecting outwardly from the outer surfaces of said shroud for interrupting the flow of gases therealong and promoting thorough intermixing of the same.

6. An apparatus for heating the atmosphere comprising:

a helicopter;

a frame adapted to be connected to the underside of said helicopter and extending outwardly on each side of said helicopter;

a heat source mounted on said helicopter for providing a flow of heated air forwardly of said helicopter, said heat source comprising at least one burner mounted on said frame on each side thereof;

said burners including means for burning a fuel supplied thereto and means for causing a flow of the heated gases from said burner in a direction forwardly of the flight path of said helicopter;

means on said frame for supporting a supply of fuel for said burners;

means for connecting said fuel supply to said burners; and control means in said helicopter operatively connected to said burners for controlling the operation of the same.

* * * * *